United States Patent [19]
Kawase et al.

[11] Patent Number: 5,851,395
[45] Date of Patent: Dec. 22, 1998

[54] VIRUS-REMOVING FILTER

[76] Inventors: Mitsuo Kawase, 7-22, Nishitatsumigaoka 1-Chome, Chita City; Yuji Kawase, NGK Aoyama-Ryo, 83, Aoyama-Cho 7-Chome, Handa City; Kazunari Yamada, 95, Matoba-Cho 2-Chome, Nakagawa-Ku, Nagoya City; Kazukiyo Kobayashi, 13-10, Wagogaoka 3-Chome, Togo-Cho, Aichi-Gun, all of Aichi Pref.; Yasuo Suzuki, 3-3-102, Sena 1-Chome, Shizuoka City, Shizuoka Pref., all of Japan

[21] Appl. No.: 771,762

[22] Filed: Dec. 20, 1996

[30] Foreign Application Priority Data

Dec. 25, 1995 [JP] Japan .................................. 7-342262
Dec. 20, 1996 [JP] Japan .................................. 8-341199

[51] Int. Cl.⁶ .................................................. B01D 39/00
[52] U.S. Cl. .............................. 210/500.27; 210/500.1; 210/500.36; 55/524; 96/4; 96/11

[58] Field of Search ......................... 210/500.1, 500.27, 210/500.36, 656, 500.35, 490; 435/5, 7, 188; 424/12; 95/43, 45; 96/4–11; 264/48–49; 55/524, DIG. 35

[56] References Cited

U.S. PATENT DOCUMENTS 3,646,346  2/1972  Catt .......................................... 436/531
4,217,338  8/1980  Quash ....................................... 436/543
4,282,315  8/1981  Luderer et al. .
4,355,102  10/1982  Quash .

FOREIGN PATENT DOCUMENTS 6-263801   9/1994  Japan .
89/01813   3/1989  WIPO .

*Primary Examiner*—Ana Fortuna
*Attorney, Agent, or Firm*—Parkhurst & Wendel, L.L.P

[57] ABSTRACT

A virus-removing filter using, as a virus-capturing body, at least one kind of sialic acid, a sialic acid derivative, and sugars, glycoproteins and glycolipids containing sialic acid and/or the sialic acid derivative.

12 Claims, 3 Drawing Sheets neuraminic acid

N-acetyl group
(widely present in animals)

N-glycolyl group
(porcin submaxilary gland)

N-acetyl-4-0-acetyl group (equine submaxilary gland)

N-acetyl-7-0-acetyl group (bovine submaxilary gland)

N-acetyl-7,9-dl-0-acetyl group (equine submaxilary gland)

neuraminic acid

N-acetyl group
(widely present in
animals)

N-glycolyl group
(porcin submaxilary
gland)

N-acetyl-4-0-acetyl
group (equine
submaxilary gland)

N-acetyl-7-0-acetyl
group (bovine
submaxilary gland)

N-acetyl-7,9-dl-0-
acetyl group (equine
submaxilary gland)

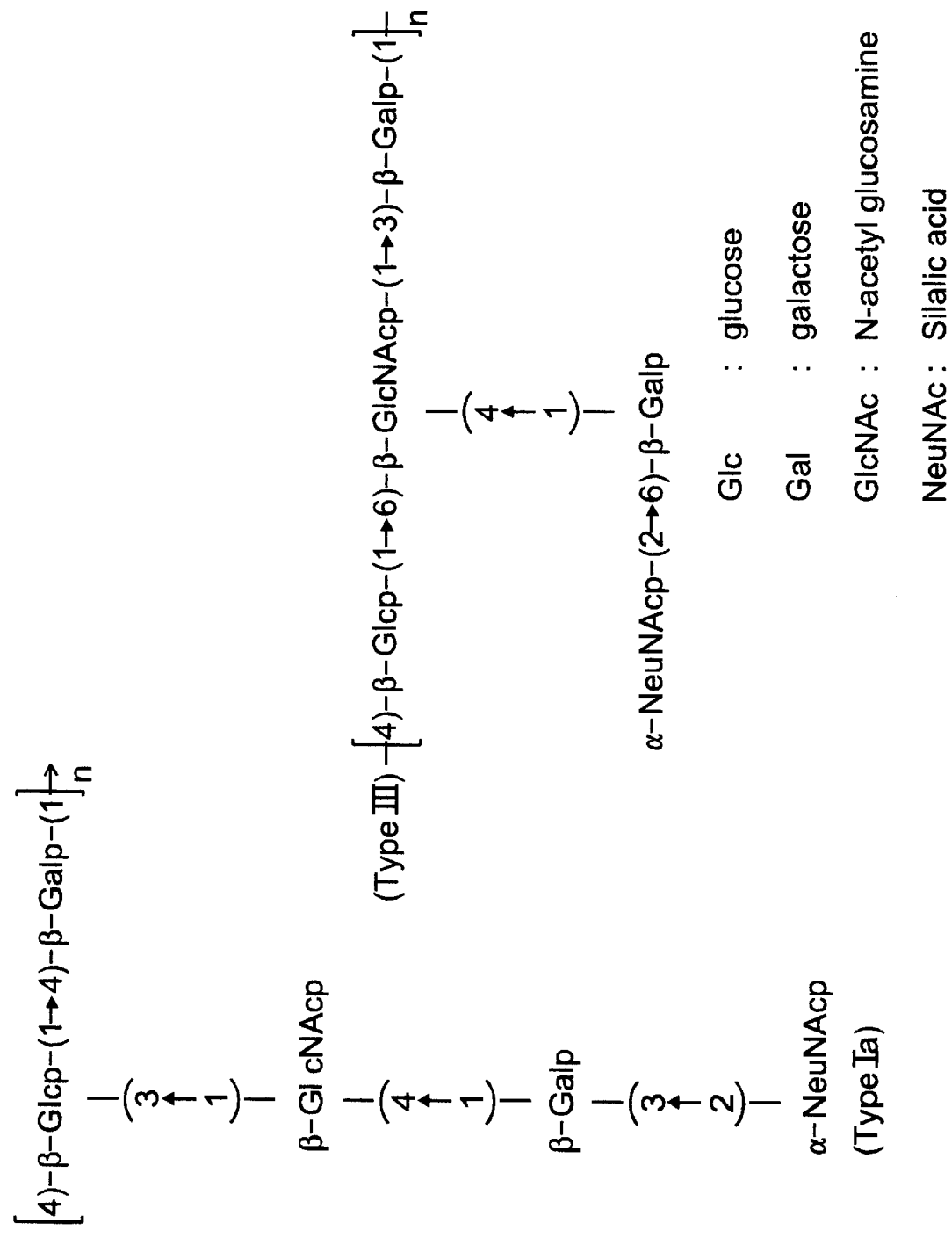

VIRUS-REMOVING FILTER

BACKGROUND OF THE INVENTION

Field of the Invention

The present invention relates to a filter capable of removing viruses such as influenza.

As a means for removing the virus suspended in the air, a technique has been conventionally known to capture the virus with a filter and inactivate the thus captured virus with ultraviolet light. However, since the ultraviolet light is harmful against the human bodies, it is difficult to use such a technique in ordinary living spaces. In addition, the ultraviolet light is likely to deteriorate the material of the filter and any accompanying equipment. Further, although gauze masks are widely used in ordinary living spaces, such gauze masks cannot capture the viruses.

SUMMARY OF THE INVENTION

The present invention is to remove the above-mentioned conventional problem, and has been accomplished to provide virus-removing filters which can be used in ordinary living space and effectively remove viruses such as influenza.

The present invention has been accomplished to attain the above object.

A first aspect of the present invention is to provide a virus-removing filter using, as a virus-capturing body, at least one kind of sialic acid, a sialic acid derivative, and sugars, glycoproteins and glycolipids containing sialic acid and/or the sialic acid derivative.

A second aspect of the present invention is to provide a virus-removing filter using, as a virus-capturing body, a substrate in which at least one kind of sialic acid, a sialic acid derivative, and sugars, glycoproteins and glycolipids containing sialic acid and/or the sialic acid derivative is impregnated or kneaded.

A third aspect of the present invention is to provide a virus-removing filter using, as a virus-capturing body, a material with which at least one kind of sialic acid, a sialic acid derivative, and sugars, glycoproteins and glycolipids containing sialic acid and/or the sialic acid derivative is covalently bonded.

A fourth aspect of the present invention is to provide a virus-removing filter using, as a virus-capturing body, a polymerized/copolymerized material which is obtained by polymerizing and/or copolymerizing styrene monomer and/or acryl amide monomer into which at least one kind of sialic acid, a sialic acid derivative, and sugars, glycoproteins and glycolipids containing sialic acid and/or the sialic acid derivative is incorporated.

These and other objects, features and advantages of the invention will be appreciated upon reading of the following description of the invention when taken in conjunction with the attached drawings, with the understanding that some modifications, variations and changes of the same could be easily made by the skilled person in the art to which the invention pertains.

BRIEF DESCRIPTION OF THE INVENTION

Reference is made to the attached drawings, wherein:

FIGS. 3 shows a separated and extracted component type 1-a sugar chain (a sugar containing sialic acid).

DETAILED DESCRIPTION OF THE INVENTION

In the following, embodiments of the preset invention will be explained in more detail.

In the present invention, at least one kind of sialic acid, a sialic acid derivative, and sugars, glycoproteins and glycolipids containing sialic acid and/or the sialic acid derivative, their covalently bonded materials and/or the polymers or copolymers containing them is used as a constituent element for capturing the viruses. Sialic acid is contained in various living things, and exists in the state that it usually constitutes cell surface layer glycolipids and is bonded to glucocide-bonded to terminals of glycoproteins or glycolipids (composite glucides). Sialic acid used in the present invention can be economically produced by a process described in NGK's Japanese patent application Laid-open No. 6-263,80-1. According to this process, sialic acid is released by hydrolyzing colominic acid produced by bacteria such as Escherichlacoli with an acid.

On the other hand, many viruses such as influenza to be captured by the present invention have proteins called "hemagglultinin" at their surfaces. It is known known that as this hemaggultinin bonds to sialic acid at surfaces of cells of an animal, the animal is infected with such viruses. That is, these viruses function to infect the calls via sialic acid as receptor at the cell surface of the animal. The present invention utilizes the above phenomenon, and is to remove the virus having the "hemaggultinin" by capturing the virus with sialic acid, its derivative or the like as or in a virus-capturing body which has been incorporated into a filter.

Figure 1:
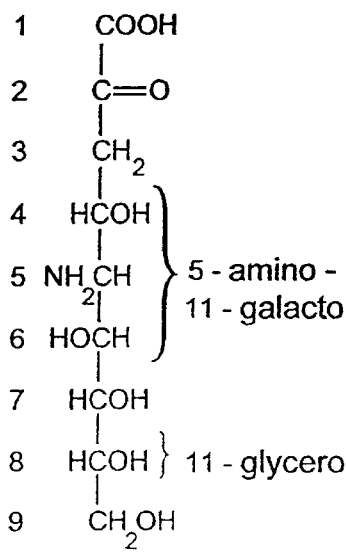
FIG. 1 shows chemical structures of some sialic acid derivatives present in nature.
Figure 1:
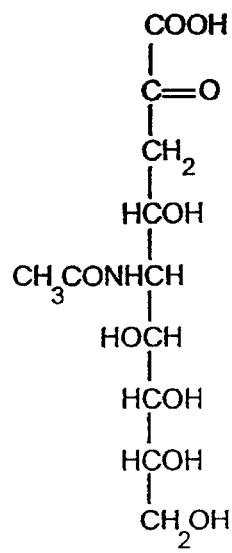
Figure 1:
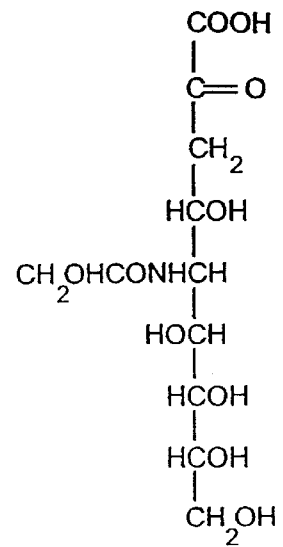
Figure 1:
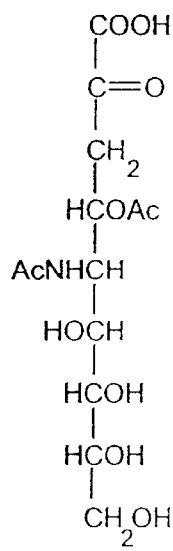
Figure 1:
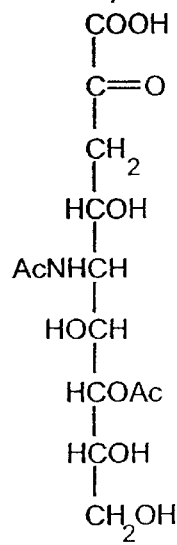
Figure 1:
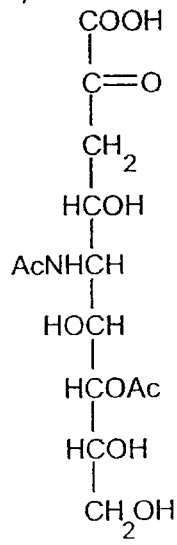

As the sialic acid derivative, a deoxy form and a dehydroxy form of sialic acid may be recited. In FIG. 1 is shown some of such sialic acid derivatives occurring in nature. As sugars containing sialic acid or its derivatives, sialyl lactose and sialyl lactosamine may be recited. As glycoproteins containing sialic acid or a sialic acid derivative, for example, mucin may be recited. As glycolipids containing sialic acid or its derivatives, for example, ganguliosid may be recited, The above-recited materials may be used singly or in combination as or in the virus-capturing body for capturing the viruses having "hemaggultinin1.

(2) A substrate in which at least one kind of sialic acid, a sialic acid derivative, sugars, glycoproteins, or glycolipids containing sialic acid and/or the sialic acid derivative is impregnated or kneaded may be also used as a virus-capturing body. If a gauze is used as the substrate, it may be used as a virus-removing mask.

(3) A material with which at least one kind of sialic acid, a sialic acid derivative, sugars, glycoproteins, or glycolipids containing sialic acid and/or the sialic acid derivative is covalently bonded may be used as a virus-capturing body. If this covalently bonded material is sandwiched in a gauze, it may be used as a virus-removing mask. In this case, the covalently bonded material in the form of powder is placed in a bag, and this bag is sandwiched with a gauze.

Figure 2:
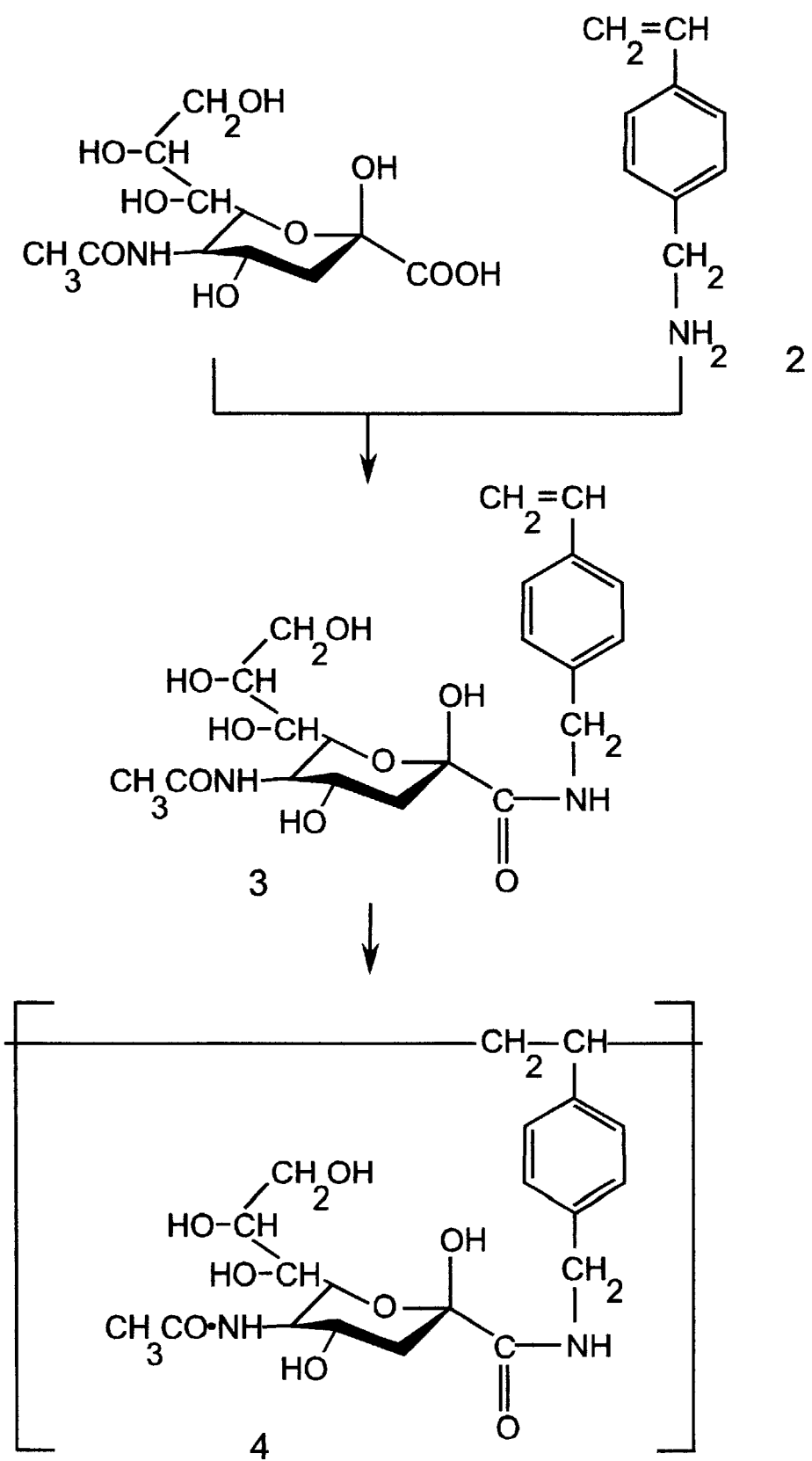
FIG. 2 shows chemical reaction formulae for the steps of producing a composite glucocide polymeric material containing sialic aicd.

(4) A polymerized and/or copolymerized material which is obtained by polymerizing and/or copolymerizing styrene monomer and/or acryl amide monomer into which at least one kind of sialic acid, a sialic acid derivative, sugars, glycoproteins, or glycolipids containing sialic acid and/or the sialic acid derivative is incorporated may be used as a virus-capturing body. FIG. 2 shows the steps in the production of the virus-capturing body using the styrene monomer. Sialic acid (1) and p-vinylbenzyl amine (2) are subjected to a condensation reaction, thereby obtaining a sialic acid-substituted styrene monomer (3). This monomer (3) is subjected to polymerization, thereby obtaining a composite sugar polymer (4). Since sialic acid or the like may be incorporated or bonded to a synthetic resin according to this process, the resulting synthetic resin may be used as a virus-removing filter or a virus-removing mask as it is or in the state that such a synthetic resin is sandwiched with a gauze. If the synthetic resin is used as it is, the resin may be used in a porous form. If the synthetic resin is used in the state that it is sandwiched with a gauze, the resin in the form of powder is, for example, placed in a bag, and this bag is sandwiched with the gauze.

(EXAMPLE 1)

*Streptococcus agalactiae* (hereinafter referred to as "B-group Streptococcus") type Ia was cultivated in a Todd-Hewitt broth containing 2% glucose and 1.5% disodium hydrogenphosphate and buffered at pH 7.0 to 7.2. A component of the type1-a sugar chain (sugar containing sialic acid) shown in FIG. 3 was separated and extracted from the resulting culture, and was dissolved into pure water, thereby preparing a 1% aqueous solution. A conventional filter (a commercially available gauze mask) was immersed in this aqueous solution, lightly dewatered, and dried to attach the extracted component thereto. Thus, the filter with the sugar containing sialic acid (hereinafter referred to as "sialic acid-containing filter 1") was obtained. Virus-removing tests were conducted by using the sialic acid-containing filter 1 and a conventional filter. The test was conducted as follows. That is, a suspended liquid was prepared by suspending A type influenza virus A/PR/8/34 (H1N1) strain in physiologic saline (0.9% aqueous solution of sodium chloride). Then, the suspended liquid was passed through each of filters, and a titer of the liquid passed was measured. The titer was measured by utilizing a phenomenon that if influenza virus attached to red blood cells, the cells cause aggregation. That is, 2-fold diluted, 4-fold diluted, 8-fold diluted, . . . aqueous solutions were prepared by diluting the suspended liquid having passed the filter with physiologic saline. A given amount of each of the thus diluted aqueous solutions was successively mixed with the same amount of a 0.4% suspended liquid of fowl red blood cells, and the titer was obtained by determining that with up to which fold diluted solution the fowl red blood cell aqueous solution caused aggregation reaction. Results are shown in the following Table 1. In this table, blank shows a titer of a raw liquid (the virus-suspended liquid before dilution).

TABLE 1

| Kind of filter | Titer |
| --- | --- |
| Blank | 512 |
| Conventional filter (one sheet) | 512 |
| Conventional filter (two sheets) | 512 |
| Sialic acid-containing filter 1 (one sheet) | 16 |
| Sialic acid-containing filter 1) two sheets) | 4 |

As is clear from the data shown in Table 1, the titer of the liquid having passed the conventional filter was the same as that of the raw liquid, and the conventional filter has completely no virus-removing effect. To the contrary, the titers of the liquid having passed the filter according to the present invention were reduced to 1/32 to 1/128 of that of the raw liquid, which means that most of the virus was removed.

(EXAMPLE 2)

"B-group Streptococcus") type III was cultivated in the same manner as in Example 1. A component of the III type sugar chain (sugar containing sialic acid) shown in FIG. 3 was separated and extracted, and was dissolved into pure water from the resulting culture, thereby preparing a 1% aqueous solution. A conventional filter was immersed in this aqueous solution, lightly dewatered, and dried to attach the extracted component thereon. Thus, the filter with the sugar containing sialic acid (hereinafter referred to as "sialic acid-containing filter 2") was obtained. Virus-removing tests were conducted by using the sialic acid-containing filter 2 and a conventional filter.

The test was conducted as follows. That is, a suspended liquid was prepared by suspending type A influenza virus A/Alchl/2/68 (H3N2) strain in physiologic saline. Then, the suspended liquid was passed through each of filters, and a titer of the liquid passed was measured in the same manner as in Example 1. Results are shown in the following Table 2. In this table, blank shows a titer of a raw liquid (the virus-suspended liquid before dilution).

TABLE 2

| Kind of filter | Titer |
| --- | --- |
| Blank | 1024 |
| Conventional filter (one sheet) | 1024 |
| Conventional filter (two sheets) | 1024 |
| Sialic acid-containing filter 1 (one sheet) | 32 |
| Sialic acid-containing filter 1) two sheets) | 4 |

As is clear from the data shown in Table 2, the titer of the liquid having passed the conventional filter was the same as that of the raw liquid, and the conventional fitler has completely no virus-removing effect. To the contrary, the titers of the liquid having passed the filter according to the present invention were reduced to 1/32 to 1/256 of that of the raw liquid, which means that most of the virus was removed.

(EXAMPLE 3)

The 1% aqueous solutions of the extracted component of the sialic acid sugar chain prepared in each of Examples 1 and 2 were mixed at a 50:50 ratio. A conventional filter was immersed into the resulting mixed solution, lightly dewatered and then dried, thereby attaching the extracted component upon the filter. Thus, the filter with the sugar containing sialic acid (hereinafter referred to as "sialic acid-containing filter 3) was obtained. Virus-removing tests were conducted by using the sialic acid-containing filter 3 and a conventional filter.

The test was conducted as follows. That is, a suspended liquid was prepared by suspending type A influenza virus A/PR/8/34 (H1N1) strain in physiologic saline. Then, the suspended liquid was passed through each of filters, and a titer of the liquid passed was measured in the same manner as in Examples 1 and 2. Results are shown in the following Table 3. In this table, blank shows a titer of a raw liquid (the virus-suspended liquid before dilution).

TABLE 3

| Kind of filter | Titer |
| --- | --- |
| Blank | 512 |
| Conventional filter (one sheet) | 512 |
| Conventional filter (two sheets) | 512 |
| Sialic acid containing filter 1 (one sheet) | 32 |
| Sialic acid containing filter 1) two sheets) | 8 |

As is clear from the data shown in Table 3, the titer of the liquid having passed the conventional filter was the same as that of the raw liquid, and the conventional filter has completely no virus-removing effect. To the contrary, the titers of the liquid having passed the filter according to the present invention were reduced to 1/16 to 1/64 of that of the raw liquid, which means that most of the virus was removed.

(EXAMPLE 4)

Virus-removing tests were conducted by using the sialic acid-containing filter 3 obtained in Example 3 and a conventional filter.

The test was conducted as follows. That is, a suspended liquid was prepared by suspending type A influenza virus A/Alchl/2/68/ (H3N2) strain in physiologic saline. Then, the suspended liquid was passed through the same manner as in Examples 1, 2 and 3. Results are shown in the following Table 4. In this table blank shows a titer of the raw liquid (the virus-suspended liquid before dilution).

TABLE 4

| Kind of filter | Titer |
|---|---|
| Blank | 1024 |
| Conventional filter (one sheet) | 1024 |
| Convontional filter (two sheets) | 1024 |
| Sialic acid-containing filter 1 (one sheet) | 64 |
| Sialic acid containing filter 1) two sheets) | 8 |

As is clear from the data shown in Table 4, the titer of the liquid having passed the conventional filter was the same as that of the raw liquid, and the conventional filter has completely no virus-removing effect. To the contrary, the titers of the liquid having passed the filter according to the present invention were reduced to 1/16 to 1/64 of that of the raw liquid, which means that most of the virus was removed.

Each of Examples 1 to 4, the tests were effected in the state that the virus was suspended in the physiologic saline. Since a similar effect can be expected with respect to the virus suspended in air, the filter according to the present invention can be used as a virus-removing mask as it is.

What is claimed is:

1. A virus-removing filter for removing air-suspended virus from air comprising a filter material allowing air to pass therethrough and thereby remove air-suspended virus from air during passage therethrough and a virus-capturing body on or within said filter material, said virus-capturing body selected from the group consisting of sialic acid, a sialic acid derivative, a sugar containing sialic acid and/or a sialic acid derivative, a glycoprotein containing sialic acid and/or a sialic acid derivative, a glycolipid containing sialic acid and/or a sialic acid derivative, and mixtures thereof.

2. The virus-removing filter of claim 1, wherein said sialic acid derivative is a deoxy form of sialic acid or a dehydroxy form of sialic acid.

3. The virus-removing filter of claim 1, wherein said filter material has a shape permitting the filter material to be placed over the nose of a wearer.

4. A virus-removing filter for removing air-suspended virus from air comprising a filter material allowing air to pass therethrough and thereby remove air-suspended virus from air during passage therethrough and a virus-capturing body attached to or on or within said filter material, said virus-capturing body being a substrate having impregnated therein or kneaded therein a member selected from the group consisting of sialic acid, a sialic acid derivative, a sugar containing sialic acid and/or a sialic acid derivative, a glycoprotein containing sialic acid and/or a sialic acid derivative, a glycolipid containing sialic acid and/or a sialic acid derivative, and mixtures thereof.

5. The virus-removing filter of claim 4, wherein said sialic acid derivative is a deoxy form of sialic acid or a dehydroxy form of sialic acid.

6. The virus-removing filter of claim 4, wherein said filter material has a shape permitting the filter material to be placed over the nose of a wearer.

7. A virus-removing filter for removing air-suspended virus from air comprising a filter material allowing air to pass therethrough and thereby remove air-suspended virus from air during passage therethrough and a virus-capturing body attached to or on or within said filter material, said virus-capturing body being a material having covalently bonded thereto a member selected from the group consisting of sialic acid, a sialic acid derivative, a sugar containing sialic acid and/or a sialic acid derivative, a glycoprotein containing sialic acid and/or a sialic acid derivative, a glycolipid containing sialic acid and/or a sialic acid derivative, and mixtures thereof.

8. The virus-removing filter of claim 7, wherein said sialic acid derivative is a deoxy form of sialic acid or a dehydroxy form of sialic acid.

9. The virus-removing filter of claim 7, wherein said filter material has a shape permitting the filter material to be placed over the nose of the wearer.

10. A virus-removing filter for removing air-suspended virus from air comprising a filter material allowing air to pass therethrough and thereby remove air-suspended virus from air during passage therethrough and a virus-capturing body attached to or on or within said filter material, said virus-capturing body being a polymerized/copolymerized material formed by polymerizing and/or copolymerizing a styrene monomer and/or an acrylamide monomer, either or both monomers having incorporated into a member selected from the group consisting of sialic acid, a sialic acid derivative, a sugar containing sialic acid and/or a sialic acid derivative, a glycoprotein containing sialic acid and/or a sialic acid derivative, a glycolipid containing sialic acid and/or a sialic acid derivative, and mixtures thereof.

11. The virus-removing filter of claim 10, wherein said sialic acid derivative is a deoxy form of sialic acid or a dehydroxy form of sialic acid.

12. The virus-removing filter of claim 10, wherein said filter material has a shape permitting the filter material to be placed over the nose of a wearer.

* * * * *

UNITED STATES PATENT AND TRADEMARK OFFICE
CERTIFICATE OF CORRECTION

PATENT NO. : 5,851,395
DATED : December 22, 1998
INVENTOR(S) : Mitsuo KAWASE et al.

It is certified that error appears in the above-indentified patent and that said Letters Patent is hereby corrected as shown below:

On the title page, item [76] Inventors:, line 10, change "3-3-102" to --8-3-102--; and

[30] Foreign Application Priority Data, change "Dec. 25, 1995" to --Dec. 28, 1995--.

Signed and Sealed this

Twenty-fifth Day of May, 1999

Attest:

Q. TODD DICKINSON

*Attesting Officer*     *Acting Commissioner of Patents and Trademarks*